United States Patent [19]

Stäubli et al.

[11] 4,035,378
[45] July 12, 1977

[54] PROCESS FOR THE PRODUCTION OF 1,3,4-THIADIAZOL-5(4H)-ONYL DITHIOPHOSPHORIC ACID ESTERS

[75] Inventors: Sebastian Stäubli, Magden; Lothar Schiener, Bettingen; Kurt Rüfenacht, Basel, all of Switzerland

[73] Assignee: Ciba-Geigy Corporation, Ardsley, N.Y.

[21] Appl. No.: 627,998

[22] Filed: Nov. 3, 1975

Related U.S. Application Data

[63] Continuation-in-part of Ser. No. 499,881, Aug. 23, 1974, abandoned, which is a continuation of Ser. No. 650,190, June 30, 1967, abandoned.

[30] Foreign Application Priority Data

July 5, 1966 Switzerland .................. 9760/66

[51] Int. Cl.² .................................. C07D 285/12
[52] U.S. Cl. ......................... 260/302 E; 424/270
[58] Field of Search ............... 260/302 E, 248 AS

[56] References Cited

U.S. PATENT DOCUMENTS

| | | | |
|---|---|---|---|
| 3,682,910 | 8/1972 | Colln | 260/248 AS |
| 3,919,129 | 11/1975 | Oswald et al. | 260/302 E |
| 3,920,671 | 11/1975 | Rufenacht | 260/302 E |

*Primary Examiner*—John M. Ford
*Attorney, Agent, or Firm*—Frederick H. Rabin

[57] ABSTRACT

1,3,4-Thiadiazol-5-(4H)-onyl-(4)-methyl dithiophosphoric acid ester of the formula

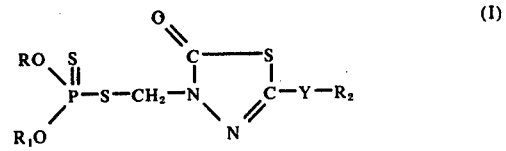

wherein each of R, R₁ and R₂ methyl or ethyl and Y represents oxygen or sulphur, are prepared by condensing a thiophosphate acid of the formula

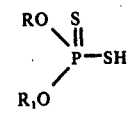

or an alkali metal or ammonium salt thereof, with a 1,3,4-thiadiazole of the formula

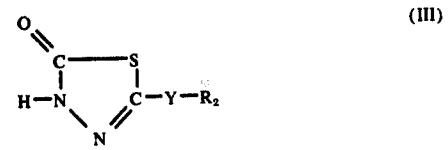

with formaldehyde in an aqueous medium consisting essentially of 60–98 wt % of sulphuric acid, the amount of sulphuric acid is at least 0.7 mol per mol of free thiophosphoric acid, if free acid is used, and 1.7 mol per mol of thiophosphoric acid salt, if a salt is used. The temperature of the reaction mixture is maintained at 15°–60° C. The process is particularly useful in the preparation of O,O-dimethyl-S-[2-methoxy-1,3,4-thiadiazol-5(4H)-onyl-(4)-methyl]-dithiophosphate (methidathion).

13 Claims, No Drawings

PROCESS FOR THE PRODUCTION OF 1,3,4-THIADIAZOL-5(4H)-ONYL DITHIOPHOSPHORIC ACID ESTERS

CROSS-REFERENCE TO RELATED APPLICATIONS

This is a continuation-in-part of application Ser. No. 499,881, filed Aug. 23, 1974, now abandoned, which is a continuation of application Ser. No. 650,190, filed June 30, 1967, now abandoned.

DETAILED DISCLOSURE

The present invention relates to a process for the production of heterocyclic thiophosphoric acid esters of formula I

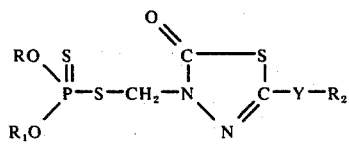

wherein the symbols R, $R_1$ and $R_2$ independently from each other represent a methyl or an ethyl radical and Y represents oxygen or sulphur.

The reaction of a thiophosphoric acid with formaldehyde and a nitrogen containing compound according to the following equation

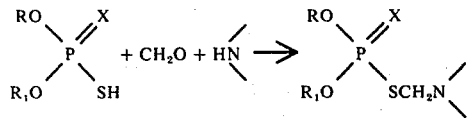

wherein X represents oxygen or sulphur, is well known.

This reaction proceeds in the absence of particular condensing agents if, in the amines, amides, lactams or ureas used as nitrogen-containing compound, the nitrogen atom entering into the new bond is much more basic than the thiophosphoric acid used as second reaction partner.

Another known process for producing similar heterocyclic thiophosphoric acid esters starting from esters of strong acids of N-hydroxy-methyl compounds of these heterocycles comprises the following sequence of reactions:

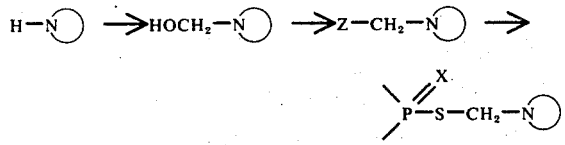

wherein
X represents oxygen or sulphur, and
Z represents halogen.
In this known multi-step process, the preparation of, in particular, the N-halogen-methyl derivatives necessitates the use of halogenating agents such as thionyl chloride, phosphorus trichloride, phosphorus oxychloride, phosphorus pentachloride, phosphorus tribromide, which are all corrosive chemicals and unpleasant to handle. Some of the N-halogen methyl derivatives are of low stability, which fact is very disadvantageous when purifying by distillation and on storing. In addition, such compounds attack the skin and mucous membranes.

The process according to the invention for producing thiophosphoric acid of formula I comprises condensing a thiophosphoric acid of formula II

wherein R and $R_1$ have the meaning given above, or an alkali metal salt or ammonium salt thereof, with a thiadiazole of formula III

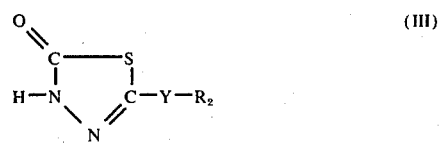

wherein Y and $R_2$ have the meaning given above, and with formaldehyde in the presence of aqueous sulphuric acid.

According to the invention about 60 to 98%, preferably 70 to 90%, by weight of sulphuric acid is used. The sulphuric acid should be present in an amount of at least 0.7 mol per mol of free thiophosphoric acid of formula II of the free and is used, on at least 1.7 mol per mol of thiophosphoric acid salt if a salt of a thiophosphoric acid of formula II is used. Preferably, the sulphuric acid is used in an amount of about 2 mol or more per mol of free thiophosphoric acid of formula II and in an amount of about 3 mol or more per mol of a salt of a thiophosphoric acid of formula II. For example, about 2.5 mol of sulphuric acid per mol of a thiophosphoric acid of formula II and about 4.5 mol of sulphuric acid per mol of a salt of a thiophosphoric acid of formula II can be advantageously used. However, an excess of sulphuric acid over these amounts has no detrimental effect on the progress of the reaction.

In the process according to the invention each of the reactants of formulae II and III can be used in excess. Preferably, however, molar equivalent or approximately equivalent amounts of the reactants of formulae II and III are introduced into the reaction to avoid a content of unreacted starting material in the final product.

The process according to the invention is carried out in a temperature range of 15° to 60° C, preferably 20° to 45° C, the reaction components being added, e.g. dropwise, to the aqueous sulphuric acid.

The formaldehyde can be used for the process according to the invention as aqueous solution or preferably in the form of paraformaldehyde.

According to a modification of the process of the present invention the thiadiazoles of formula III are first reacted with formaldehyde to obtain the corresponding 4-hydroxymethyl-1,3,4,-thiadiazoles which are subsequently condensed with a thiophosphoric acid of formula II or a salt thereof in the presence of sulphuric acid under the conditions described above. Most of the heterocyclic thiophosphoric acid esters of formula I which can be produced by the process according to the invention are known compounds. They are of great importance as active substances in pest control as described in detail in U.S. Pat. Nos. 3,230,230 and 3,240,668. Particularly effective as insecticides are O,O-dimethyl-S-[2-methoxy-1,3,4-thiadiazol-5(4H)-onyl-(4)-methyl]-dithiophosphate (methidathion) and its O,O-diethyl analogue.

A principal advantage resulting from the process of the instant invention is that the product esters are obtained in higher yields than has heretofore been possible. Yields obtainable using paraformaldehyde (preference) are in the range of 70 to 90% of the theoretical amount.

Condensation reactions of the heterocyclic compound 1,2,3-benzotriazin-4-(3H)-one (benzazimide) with a thiophosphoric acid and formaldehyde in the presence of concentrated hydrochloric acid are known from U.S. Pat. No. 3,682,910. When the heterocyclic compound is 1,3,4-thiadiazol-5-(4H)-one as in the process of the present invention, it has been found that the high yields of ester product are obtainable only when the reaction medium is the concentrated sulphuric acid called for in this invention. Replacement of the sulphuric acid by another strong acid, such as hydrochloric acid, results in significantly lower yields. In contrast, when the heterocycle is 1,2,3-benzotriazin-4(3H)-one, the use of sulphuric acid in place of the hydrochloric acid of U.S. Pat. No. 3,682,910 decreases the product yield.

The following non-limitative examples serve to illustrate the invention further and to shown its advantages. Throughout the specification and in the appended claims, where not stated otherwise, parts and percentages are given by weight and the temperatures are given in degrees Centigrade.

EXAMPLE 1

Process of This Invention

32 Parts of O,O-dimethyl-dithiophosphoric acid are added dropwise to a mixture of 82 parts of concentrated sulphuric acid and 18 parts of water, the addition being made at room temperature. Then 26 parts of 2-methoxy-1,3,4,-thiadiazol-5(4H)-one are added. Then 17 parts of a 37% aquous formaldehyde solution are added dropwise within 1 hour at 30°. The mixture is stirred for another 2 hours at 30°, 200 parts of water are added, the oily phase, which however, soon solidifies, is separated and, after recrystallisation from methanol, 37 parts of O,O-dimethyl-S-[2-methoxy-1,3,4-thiadiazol-5(4H)-onyl-(4)-methyl]-dithiophosphate are obtained, M.P. 39°–40° C. The yield is 62.5% of the theoretical amount. This somewhat "low" figure is due in the use of aqueous formaldehyde which diluted the sulphuric acid concentration from 82% to 74%. It is nevertheless considerably higher then is obtained using paraformaldehyde and concentrated hydrochloric or hydrobromic acid.

EXAMPLE 2

Process of This Invention

First, 39 parts of potassium salt of O,O-dimethyl-dithiophosphoric acid, then 26 parts of 2-methoxy-1,3,4-thiadiazol-5(4H)-one were added to a mixture of 64 parts of concentrated sulphuric acid and 16 parts of water the additions being made at 25°–30° C, and finally at 30° C, 6 parts of pulverulent paraformaldehyde were slowly added in small portions. The mixture was stirred for another 3 hours at 30° C, 200 parts of water were then added, the whole was cooled, the crystalline precipitate was isolated and, after recrystallisation from methanol, 50 parts of O,O-dimethyl-S-[2-methoxy-1,3,4,-thiadiazol-5(4H)-onyl-(4)-methyl]-dithiophosphate were obtained, M.P. 39°–40° C. The yield is 84.5% of the theoretical amount.

EXAMPLE 3

Process of This Invention

37 Parts of O,O-diethyl-dithiophosphoric acid are added dropwise to a mixture of 60 parts of concentrated sulphuric acid and 20 parts of water. 26 Parts of 2-methoxy-1,3,4-thiadiazol-5(4H)-one are added quickly and then, at 30° C, 6 parts of pulverulent paraformaldehyde are added within 2 hours. The mixture is stirred for another 2 hours at 30° C, 200 parts of water are added, the mixture is cooled and the crystalline precipitate is isolated. After recrystallization from methanol., 53 parts of O,O-diethyl-S-[2-methoxy-1,3,4-thiadiazol-5(4H)-onyl-(4)-methyl]-dithiophosphate are obtained, M.P. 43°–44° C. The yield is 81.5% of the theoretical amount.

EXAMPLE 4

Process of This Invention

First, 39 parts of potassium salt of O,O-dimethyl-dithiophosphoric acid and then 30 parts of 2-methylthio-1,3,4-thiadiazol-5(4H)-one are added to a mixture of 64 parts of concentrated sulphuric acid and 16 parts of water while cooling and, finally, at 30° C, 6 parts of paraformaldehyde are added within 2 hours. The mixture is stirred for another 2 hours at 30° C, 200 parts of water are added, the oil which separates is taken up in ether, the ether solution is washed acid free with sodium hydrogen carbonate solution and, after drying and distilling off the ether, 57 parts of O,O-dimethyl-S[2-methylthio-1,3,4-thiadiazol-5(4(H)-onyl(4)-methyl]-dithiophosphate are obtained as a yellow oil. After recrystallisation from methanol, it melts at 28°–29° C. The yield is 88% of the theoretical amount.

EXAMPLE 5

Process of This Invention

First, 41 parts of potassium salt of O,O-dimethyl-dithiophosphoric acid are added to a mixture of 64 parts of concentrated sulphuric acid and 16 parts of water while cooling gently and then, at 30° C, 35 parts of 4-hydroxymethyl-2-ethoxy-1,3,4-thiadiazol-5(4H)-one are slowly added. The mixture is stirred for another 3 hours at 30°, then cooled and 80 parts of water are added dropwise. The crystalline precipitate is isolated and recrystallised from methanol. In this way 54 parts of O,O-dimethyl-S-[2-ethoxy-1,3,4-thiadiazol-5(4H)-onyl-(4)-methyl]-dithiophosphate are obtained, M.P. 50°–51° C. The yield is 86% of the theoretical amount.

EXAMPLE 6

Process Using Hydrochloric Acid

First, 39 parts of potassium salt of O,O-dimethyl-dithiophosphoric acid and then 26 parts of 2-methoxy-1,3,4-thiadiazol-5(4H)-one are added to 100 parts of concentrated aqueous hydrochloric acid (d = 1.19), the additions being made at 25°–30°, and finally, at 30°, 6 parts of paraformaldehyde are added in small portions. The mixture is stirred for 3 hours at 30°, then 100 parts of water are added, the crystalline precipitate is isolated and, after recrystallisation from methanol, 31 parts of O,O-dimethyl-S-[2-methoxy-1,3,4-thiadiazol-5(4H)-onyl-(4)-methyl]-dithiophosphate are obtained, M.P. 39°–40°. The yield is 51% of the theoretical amount.

EXAMPLE 7

Process Using Hydrobromic Acid

First, 39 parts of potassium salt of O,O-dimethyl-dithiophosphoric acid and then 26 parts of 2-methoxy-1,3,4-thiadiazol-5(4H)-one are added to 100 parts of an about 48% aqueous hydrobromic acid, the addition being made with gentle cooling. Finally, at 30°, 6 parts of pulverulent paraformaldehyde are added within 1 hour slowly. The mixture is stirred for 3 hours at 30°, 100 parts of water are added, the lumpy precipitate is isolated and, after recrystallisation from methanol, 25 parts of O,O-dimethyl-S-[2-methoxy-1,3,4-thiadiazol-5(4H)-onyl-(4)-methyl]-dithiophosphate are obtained, M.P. 39°–40°. The yield is 41% of the theoretical amount.

A comparison of Examples 1, 2, 6 and 7, all showing the production of O,O-dimethyl-S-[2-methoxyl-1,3,4-thiadiazol-5(4H)-onyl-(4)-methyl]-dithiophosphate, illustrates the advantages of this invention.

TABLE I

| Example No. | Acid — concentration | Yield |
|---|---|---|
| 1 | Sulphuric — 82–74 % | 62,5 % |
| 2 | Sulphuric — 80 % | 84,5 % |
| 6 | Hydrochloric — 37 % | 51 % |
| 7 | Hydrobromic — 48 % | 41 % |

EXAMPLE 8

Process Using 1,2,3-benztriazin-4(3H)-one and Sulphuric Acid

First, 39 parts of potassium salt of O,O-dimethyl-dithiophosphoric acid are added to a mixture of 90 parts of concentrated sulphuric acid and 10 parts of water, the addition being made while cooling, then 29 parts of 1,2,3-benztriazin-4(3H)-one are added and, finally, 6 parts of pulverulent paraformaldenhyde are slowly added in small portions. The mixture is stirred for another 3 hours at 35°, 200 parts of water are then added dropwise the mixture is cooled, the crystalline precipitate is isolated and, after recrystallisation from methanol, 31 parts of O,O-dimethyl-S-[1,2,3-benztriazin-4(3H)-onyl-(3)-methyl]-dithlophosphate are obtained, M.P. 70°–72°. The yield is 49.5% of the theoretical amount.

EXAMPLE 9

Process Using 3-hydroxymethyl-1,2,3-benztriazin-4(3H)-one and Sulphuric Acid

First, 39 parts of potassium salt of O,O-dimethyl-dithiophosphoric acid are added to mixture of 90 parts of concentrated sulphuric acid and 10 parts of water and then 35 parts of 3-hydroxymethyl-1,2,3,-benztriazin-4(3H)-one are added in portions, the additions being made at 30°–35° while cooling. The mixture is stirred for another 2 hours at 35°, then 200 parts of water are added dropwise while cooling, the crystalline precipitate is isolated and, after recrystallisation from methanol, 38 parts of O,O-dimethyl-S-[1,2,3-benztriazin-4(3H)-onyl-(3)-methyl]-dithiophosphate are obtained, M.P. 71°–72°. The yield is 60.5% of the theoretical amount.

EXAMPLE 10

Process Using 1,2,3-benztriazin-4(5H)-one and Hydrochloric Acid

First 37 parts of ammonium salt of O,O-dimethyl-dithiophosphoric acid and then 29.5 parts of 1,2,3-benztriazin-4(3H)-one are added to 100 parts of concentrated aqueous hydrochloric acid (d = 1,19), the addition being made at 25°–30° C. Subsequently 6.3 parts of pulverulent paraformaldehyde are added at 35°–40° in small portions and the resulting mixture is stirred at 35°–40° for 3 hours. After cooling and addition of 150 ml of water the crystalline precipitate is isolated and, after recrystallisation from methanol 45 parts of O,O-dimethyl-S-[1,2,3-benztriazin-4(3H)-onyl-(3)-methyl]-dithiophosphate are obtained, M.P. 70°–71.5° C. The yield is 71% of the theoretical amount.

What is claimed is:

1. A process for the production of a 1,3,4-thiadiazol-5-(4H)-onyl-(4)-methyl dithiophosphoric acid ester of the formula

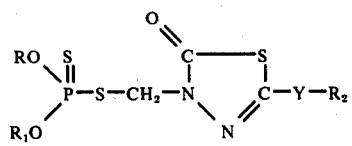

wherein each of R, $R_1$ and $R_2$ represents methyl or ethyl and Y represents oxygen or sulphur, comprising condensing a thiophosphoric acid of the formula

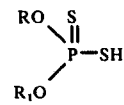

or an alkali metal or ammonium salt thereof, with a thiadiazole of the formula

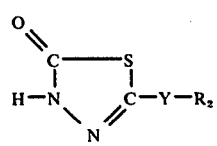

and with formaldehyde in an aqueous medium comprising sulphuric acid in concentration of from about 60 to 98%, the amount of sulphuric acid being at least 0.7 mol per mol of free thiophosphoric acid if free thiophosphoric acid is used or at least 1.7 mol per mol of thiophosphoric acid salt if a salt is used, and maintaining the temperature of the reaction mixture in the range of about 15° to 60° C.

2. A process as claimed in claim 1 wherein the aqueous medium consists essentially of 70 to 90% sulphuric acid.

3. A process as claimed in claim 1 wherein the amount of sulphuric acid in the aquous medium is at least 2 mol per mol of free thiophosphoric acid if free acid is used and about 3 mol per mol of the salt of the thiophosphoric acid if a salt is used.

4. A process as claimed in claim 3 wherein the amount of sulphuric acid in the aqueous medium is about 2.5 mol per mol of free thiophosphoric acid if free acid is used and about 4.5 mol per of the salt of the thiophosphoric acid if a salt is used.

5. A process as claimed in claim 1 which is carried out in a temperature range of 20° to 45° C.

6. A process as claimed in claim 1 wherein the thiophosphoric acid or salt thereof and the thiadiazole are used in molar equivalent amounts.

7. A process as claimed in claim 1 wherein the formaldehyde is used in the form of paraformaldehyde.

8. A process as claimed in claim 1 in which the thiophosphoric acid or salt thereof, the thiadiazole and formaldehyde are added to an aqueous medium consisting essentially of sulphuric acid.

9. A process as claimed in claim 1 in which the thiadiazole is first reacted with formaldehyde to obtain the corresponding 4-hydroxymethyl-1,3,4-thiadiazole, which is subsequently added, together with the thiophosphoric acid or salt thereof to an aquous medium consisting essentially of sulphuric acid.

10. A process for the production of a 1,3,4-thiadiazol-5(4H)-onyl-(4)-methyl dithiophosphate of the formula

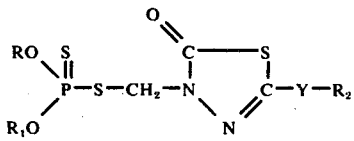

wherein each of R, $R_1$ and $R_2$ represents methyl or ethyl and Y represents oxygen or sulphur, comprising adding a thiophosphoric acid of the formula

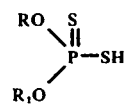

or an alkali metal or ammonium salt thereof, a thiadiazole of the formula

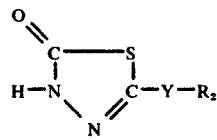

and paraformaldehyde to an aqueous medium consisting essentially of about 60 to 98% of sulphuric acid, the amount of sulphuric acid being at least 2 mol per mol of free thiophosphoric acid if free thiophosphoric acid is used or at least 3 mol per mol of thiophosphoric acid salt if a salt is used, and maintaining the temperature of the reaction mixture in the range of about 20° to 45° C.

11. A process as claimed in claim 10 wherein the thiophosphoric acid or salt thereof and the thiadiazole are used in approximately molar equivalent amounts.

12. A process as claimed in claim 11 wherein R, $R_1$ and $R_2$ are methyl and Y is oxygen.

13. A process as claimed in claim 12 wherein R and $R_1$ are ethyl, $R_2$ is methyl and Y is oxygen.

* * * * *